(12) United States Patent
Sukumaran et al.

(10) Patent No.: US 11,292,716 B2
(45) Date of Patent: Apr. 5, 2022

(54) PHOTO-CATALYTIC SPLITTING OF WATER USING SELF-ASSEMBLED METALLOPORPHYRIN 2D-SHEETS

(71) Applicant: COUNCIL OF SCIENTIFIC & INDUSTRIAL RESEARCH, New Delhi (IN)

(72) Inventors: Santosh Babu Sukumaran, Pune (IN); Ranjeesh Karayamkodath Chandran, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/853,870

(22) Filed: Apr. 21, 2020

(65) Prior Publication Data

US 2020/0247668 A1     Aug. 6, 2020

Related U.S. Application Data

(63) Continuation-in-part of application No. 16/465,918, filed as application No. PCT/IN2017/050560 on Nov. 30, 2017.

(30) Foreign Application Priority Data

Dec. 2, 2016 (IN) .............................. 201611041205
Feb. 5, 2020 (IN) .............................. 202013004941

(51) Int. Cl.
*C07D 487/22* (2006.01)
*C01B 3/04* (2006.01)
*B01J 31/18* (2006.01)
*B01J 35/00* (2006.01)
*B01J 23/42* (2006.01)

(52) U.S. Cl.
CPC ............. *C01B 3/042* (2013.01); *B01J 23/42* (2013.01); *B01J 31/1815* (2013.01); *B01J 35/004* (2013.01); *C07D 487/22* (2013.01); *B01J 2531/025* (2013.01); *B01J 2531/26* (2013.01); *B01J 2531/845* (2013.01); *B01J 2531/847* (2013.01); *C01B 2203/1041* (2013.01)

(58) Field of Classification Search
CPC .................................................. C07D 487/22
See application file for complete search history.

(56) References Cited

FOREIGN PATENT DOCUMENTS

WO     2018/100588 A1     6/2018

OTHER PUBLICATIONS

Ding et al., "An n-Channel Two-Dimensional Covalent Organic Framework," American Chemical Society, (2011) p. 14510-14513.
Jia et al., "Pyrolyzed Cobalt Porphyrin-Based Conjugated Mesoporous Polymers As Bifunctional Catalysts For Hydrogen Production And Oxygen Evolution In Water" Chemical Communications, (2016) 52, p. 13483-13486.
Neti et al., "Synthesis of a Phthalocyanine 2D Covalent Organic Framework," Cryst. Eng. Comm, (2013) 15, 7157-7160.
Ma et al., "An Efficient Electrocatalyst for Oxygen Reduction Reaction Derived from a Co-Porphyrin-Based Covalent Organic Framework," published in Electrochemistry Communications; Mar. 2015; 52, pp. 53-57.
Wang et al., "Two-Dimensional Porphyrin- and Phthalocyanine-Based Covalent Organic Frameworks," Chinese Chemical Letters, Aug. 2016, 27 (8), pp. 1376-1382.
You et al. "High-Performance Overall Water Splitting Electrocatalysts Derived from Cobalt-Based Metal-Organic Frameworks" Chem. Mater., (2015) 27(22), pp. 7636-7642.
Ashwell et al., "Aggregation-Induced Linear and Non-Linear Optical Properties of Four Hydroxy-Substituted Analogues of 2,[4-Bis[Dibutylaminio)phenyl]Squaraine," An Australian Journal of Chemistry, vol. 51, No. 7, Jul. 13, 1998; pp. 599-604.
International Search Report and Written Opinion for International Application No. PCT/IN2017/050560; International Filing Date—Nov. 30, 2017; dated Mar. 16, 2018; 11 pages.
Nagai et al., "A Squaraine-Linked Mesoporous Covalent Organic Framework," Angewandte Chemie International Edition, vol. 52, No. 13; Mar. 25, 2013, pp. 3770-3774.
Zhang et al., "Bottom-Up Approach to Engineer Two Covalent Porphyrinic Frameworks as Effective Catalysts for Selective Oxidation," Catalysis Science & Technology, vol. 5, No. 1, Sep. 24, 2015; pp. 101-104.
Ma et al, "An Efficient Electrocatalyst for Oxygen Reduction Reaction Derived from a Co-Porphyrin-based Covalent Organic Framework " Electrochemistry Communications, No. 52, (2015) pp. 53-57.
You et al. "High Performance Overall Water Splitting Electrocatalysts Derived from Cobalt-Based Metal-Organic Frameworks," Chemistry of Materials, (2015), pp. 1-10.

*Primary Examiner* — Brian E Mcdowell
(74) *Attorney, Agent, or Firm* — Cantor Colburn LLP

(57) ABSTRACT

The present invention discloses a process for the photocatalytic splitting of water using self-assembled metalloporphyrin 2D-sheet of formula (I) to form hydrogen and oxygen.

10 Claims, 10 Drawing Sheets

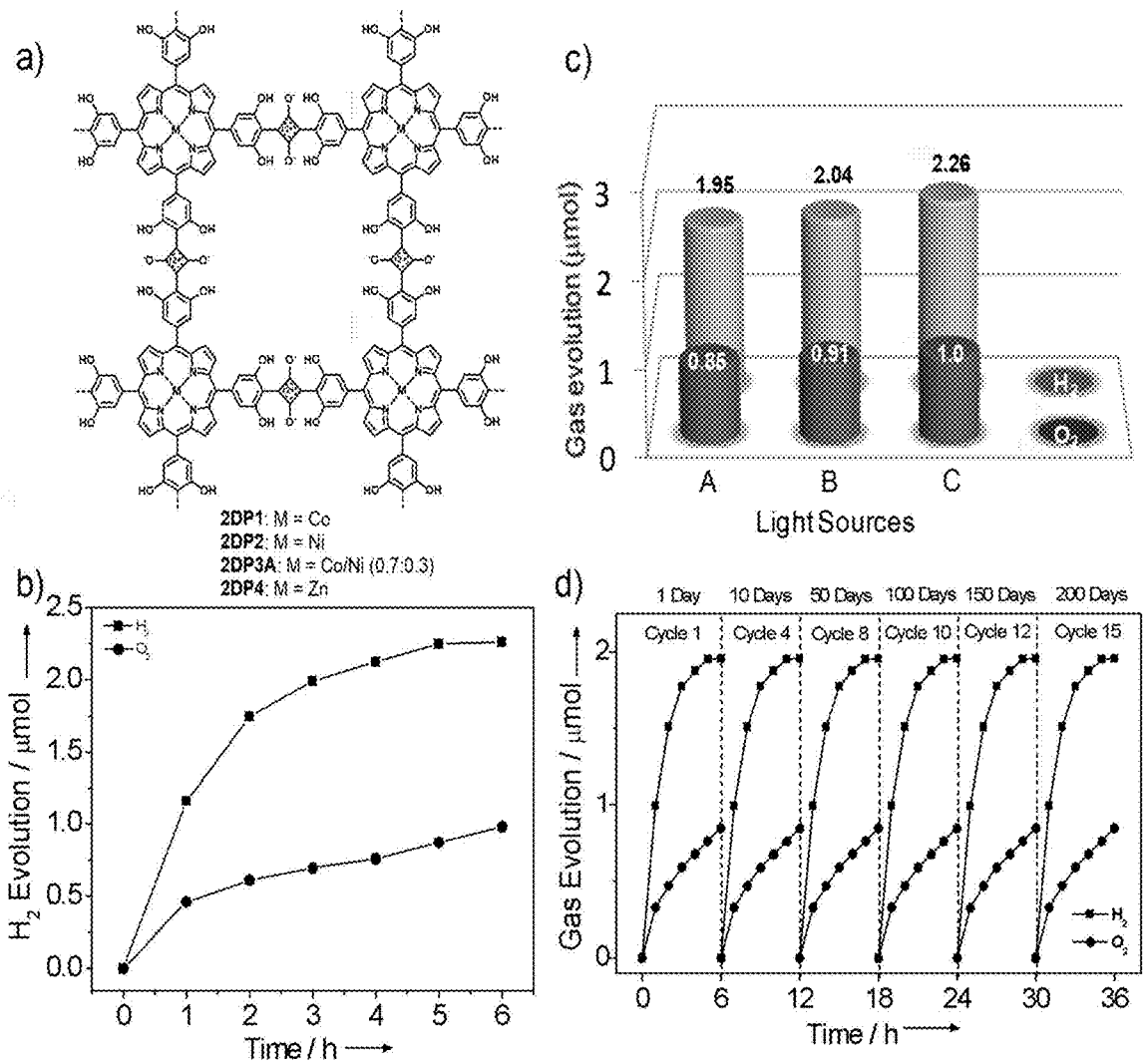
Fig: 1

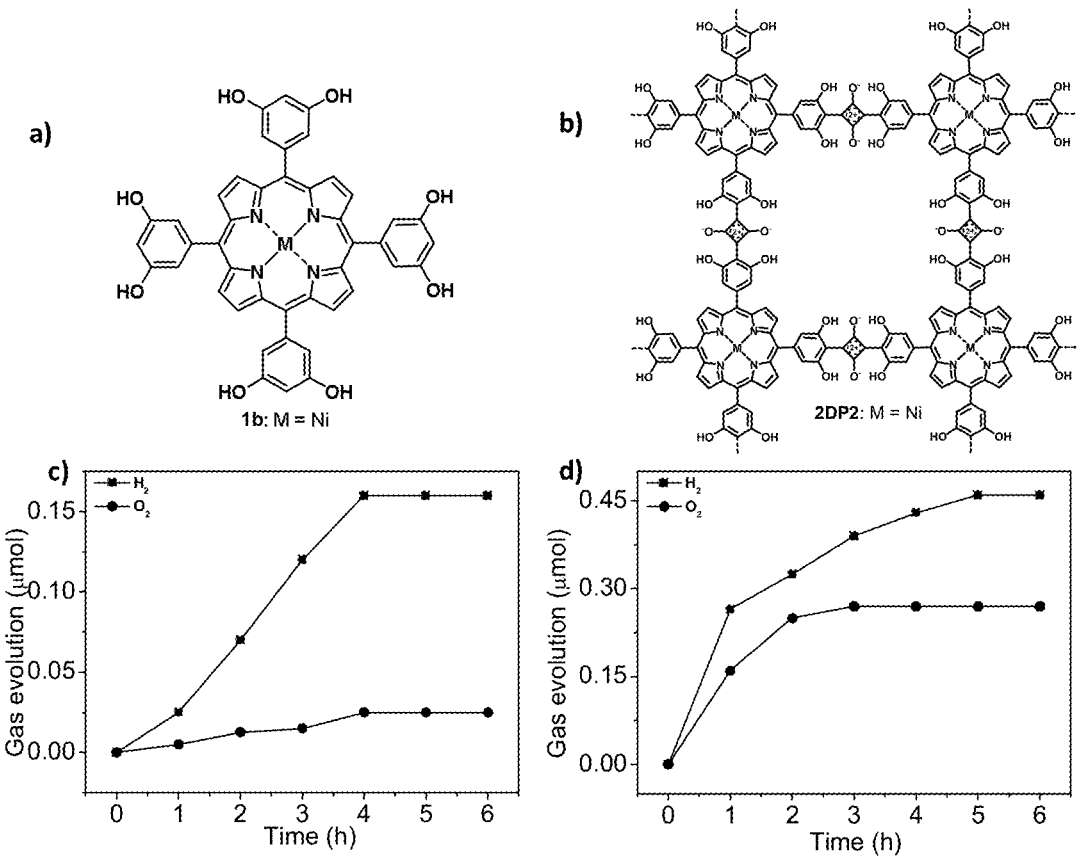
Fig: 2

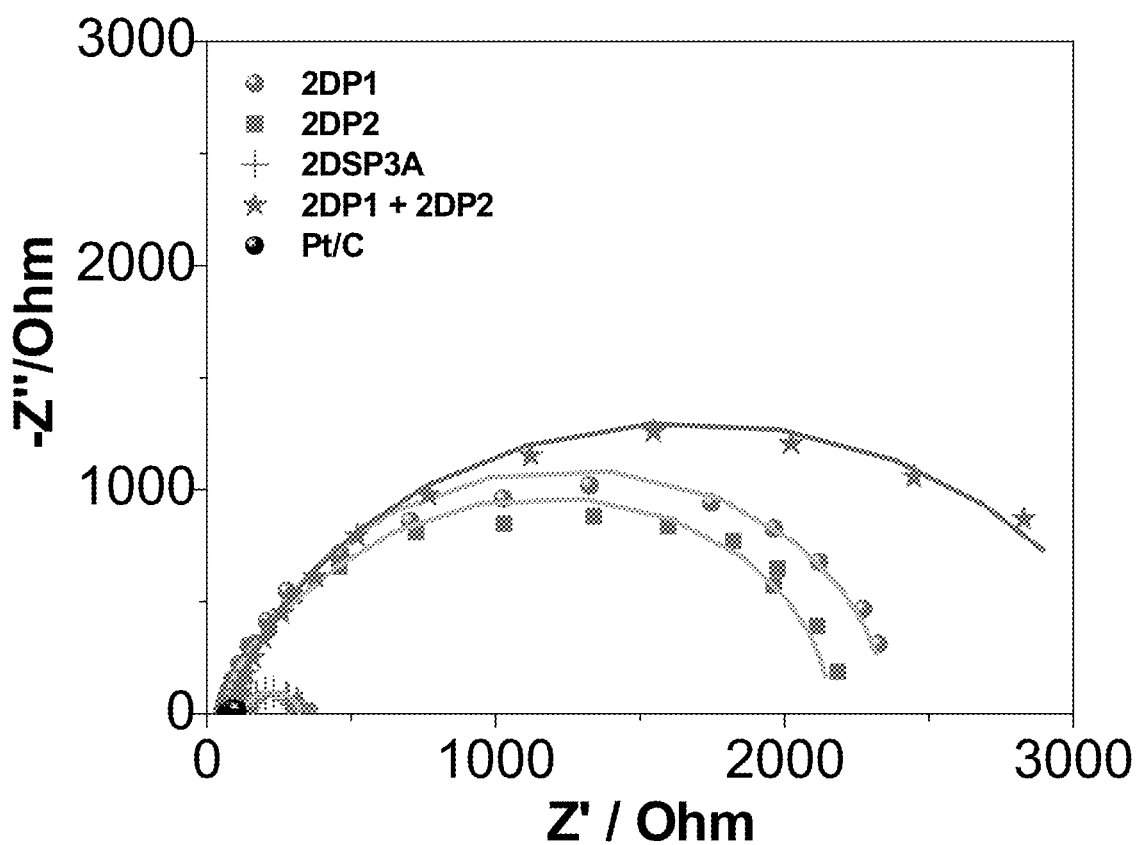
Fig: 3

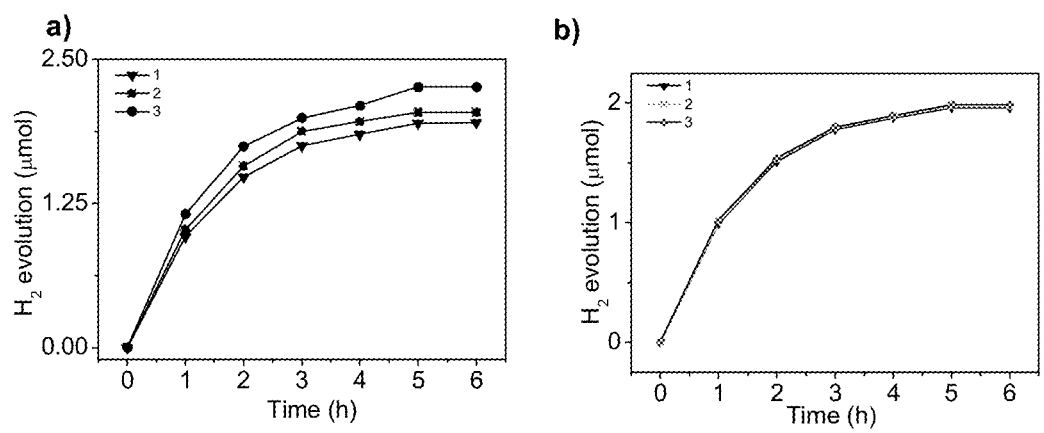
Fig: 4

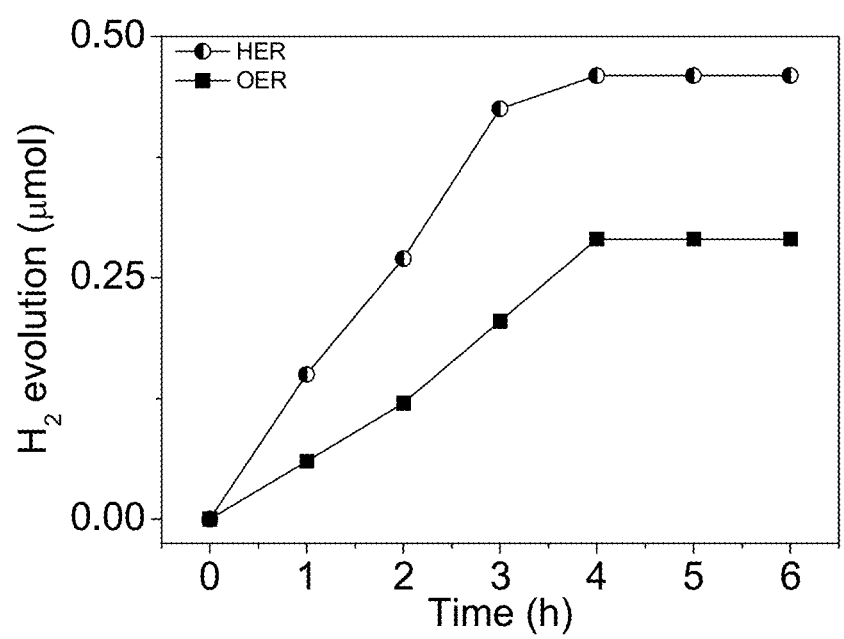
Fig:5

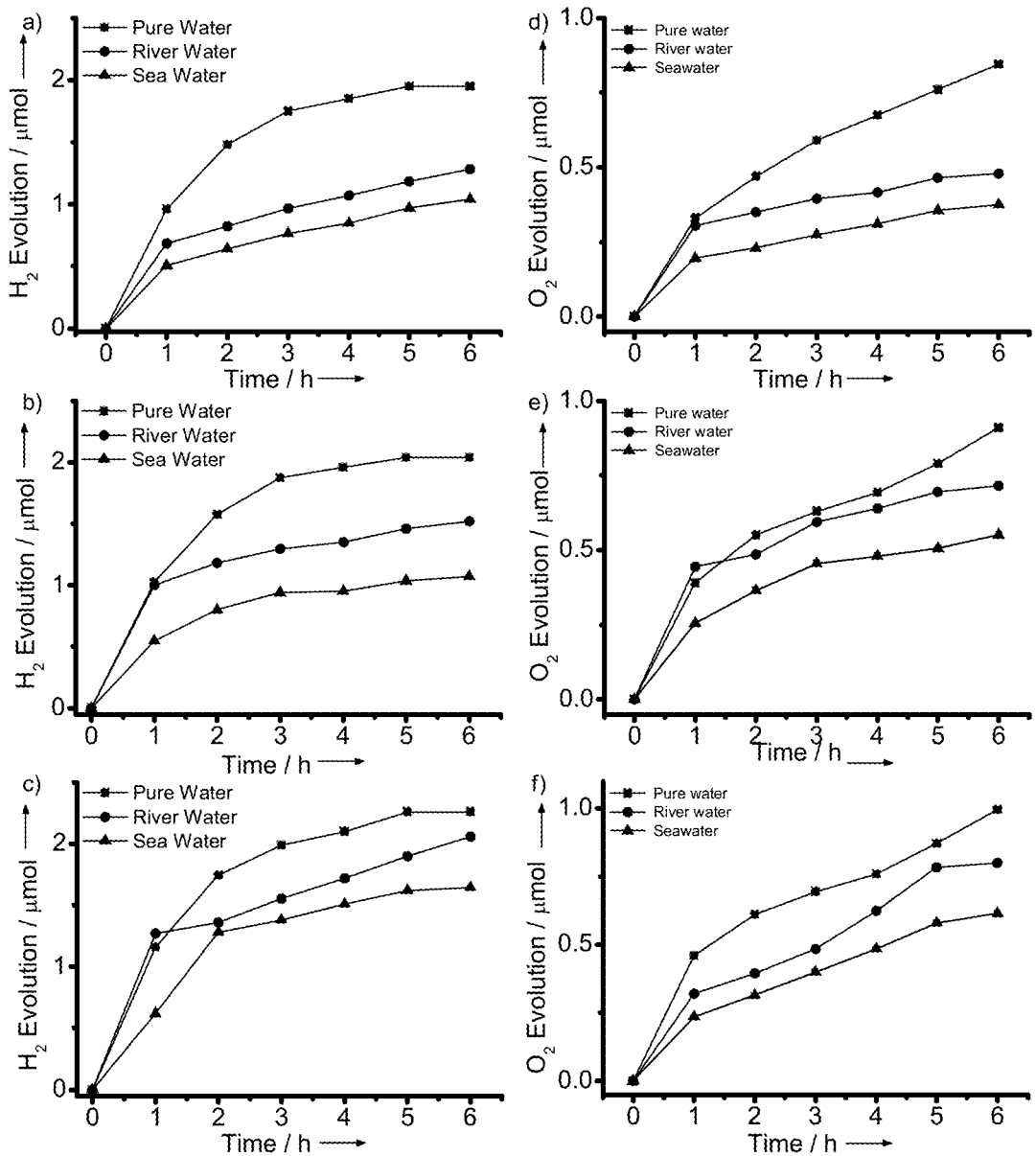
Fig: 6

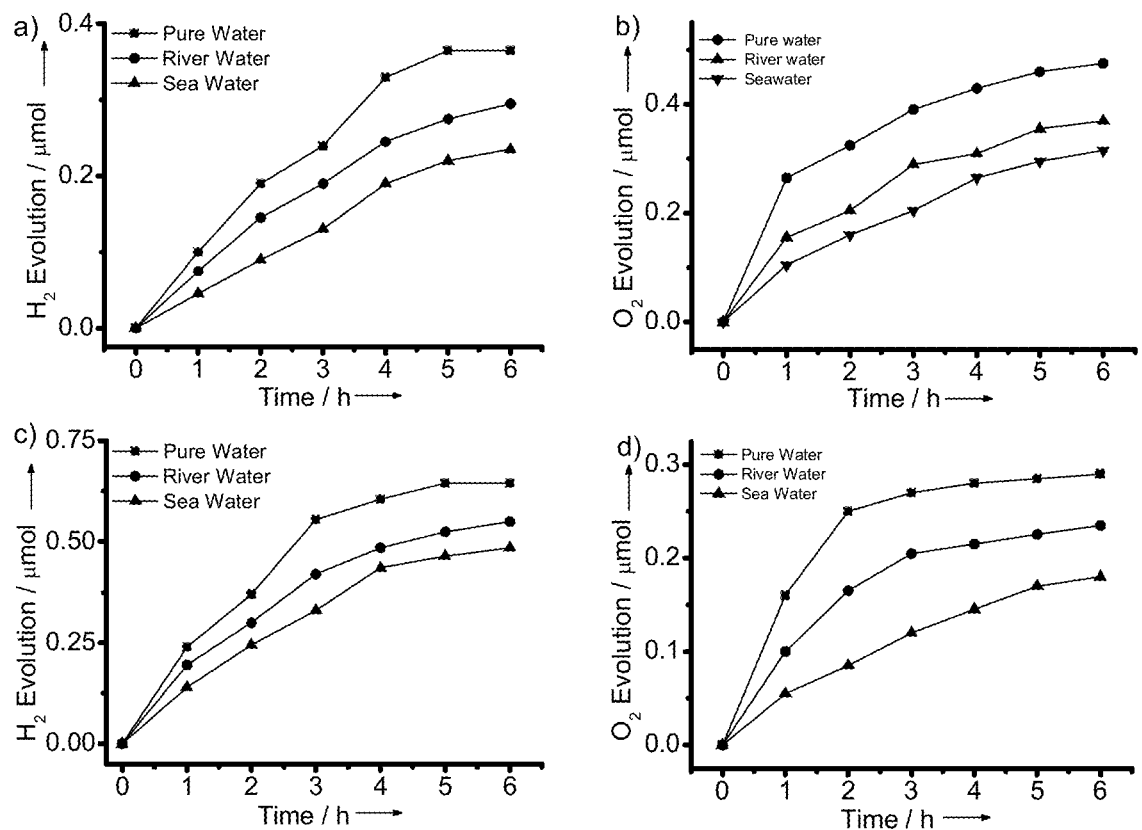
Fig: 7

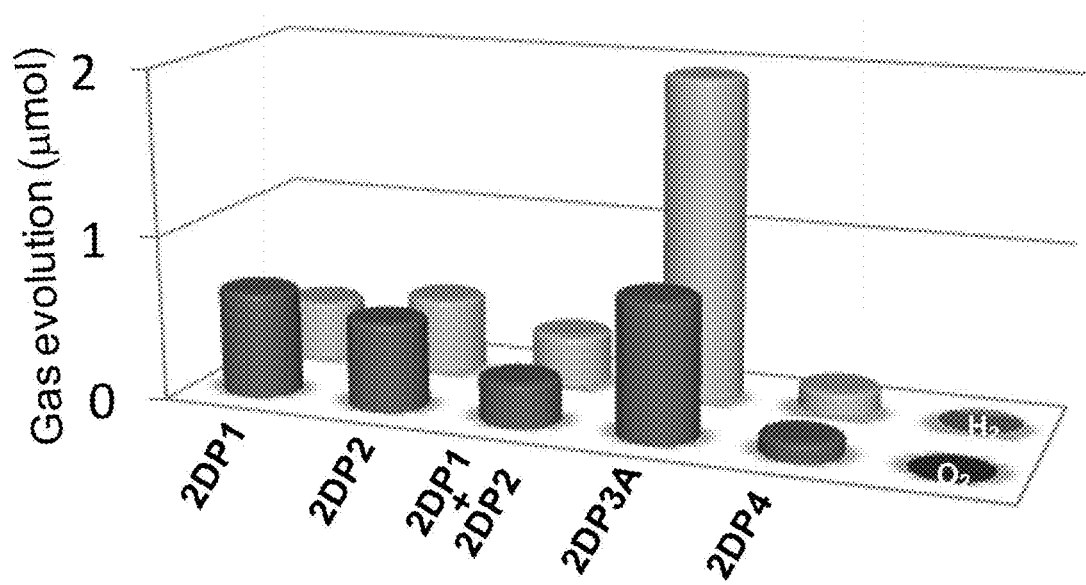
Fig:8

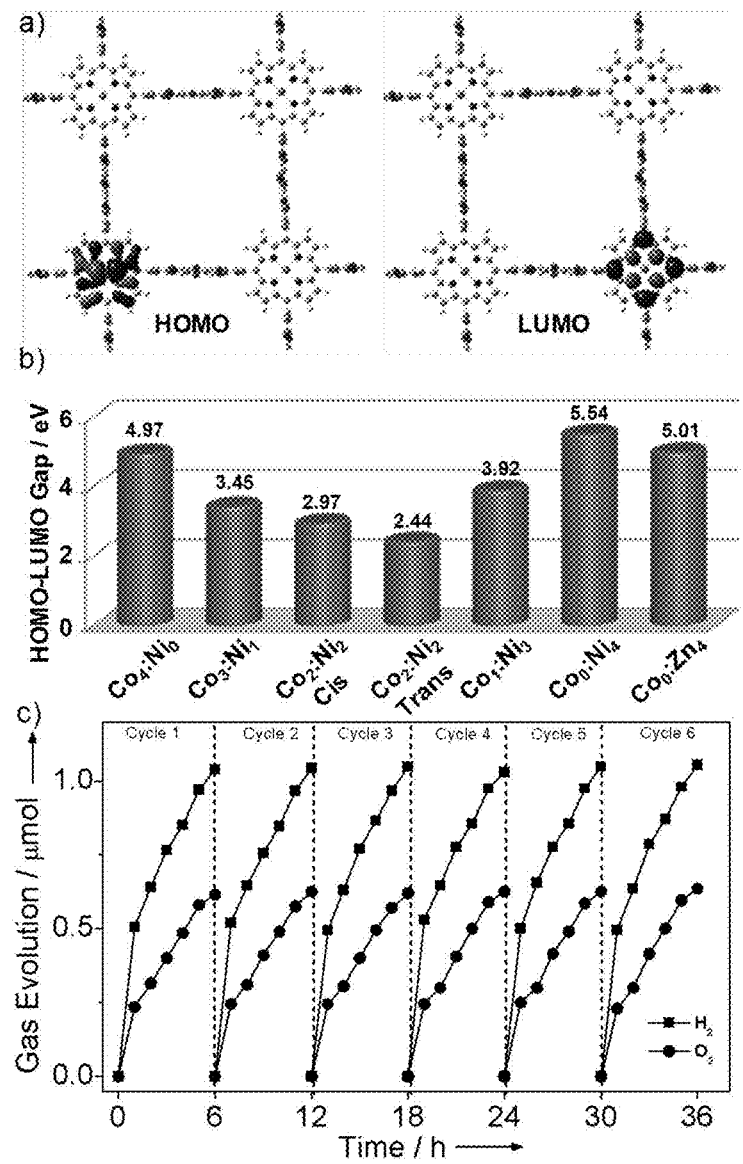
Fig:9

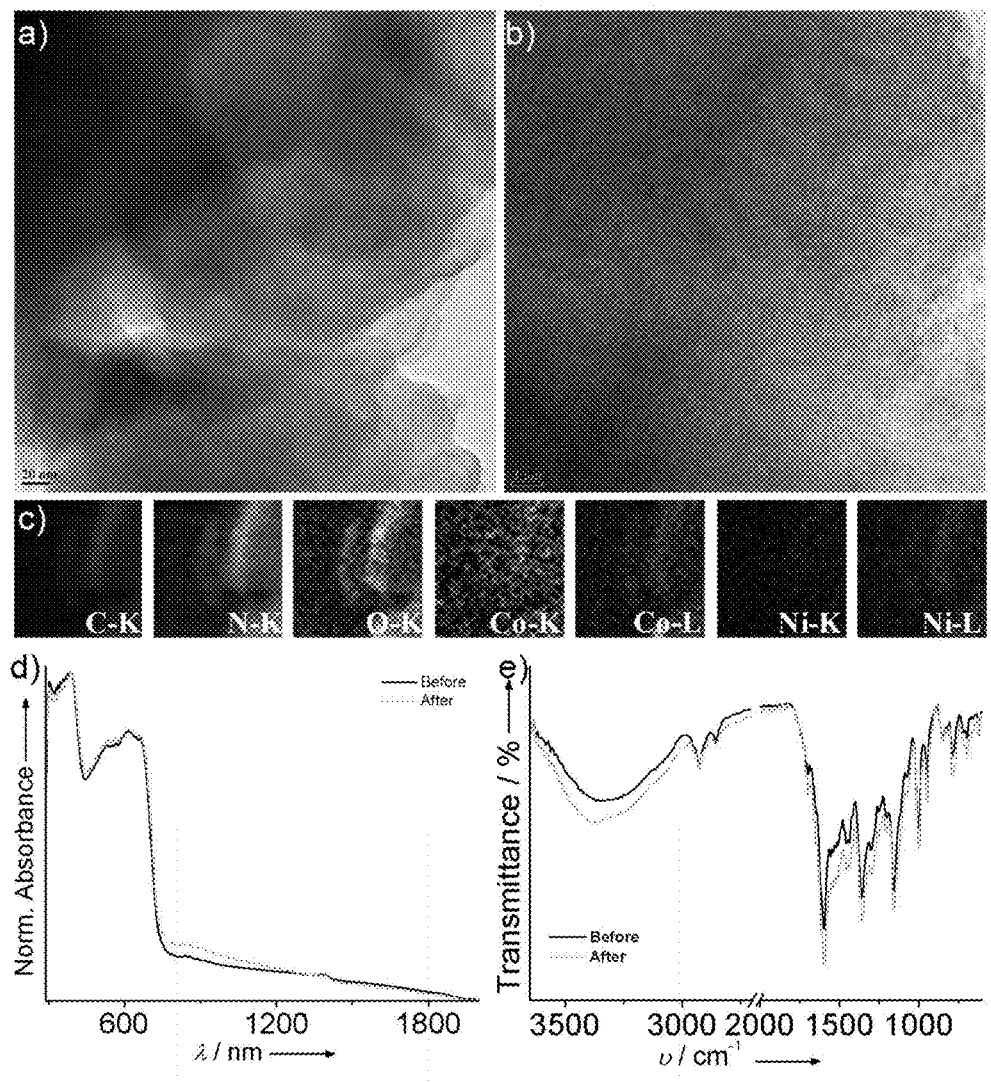
Fig:10

PHOTO-CATALYTIC SPLITTING OF WATER USING SELF-ASSEMBLED METALLOPORPHYRIN 2D-SHEETS

CROSS REFERENCE TO RELATED APPLICATIONS

This application is a continuation-in-part of U.S. application Ser. No. 16/465,918, filed May 31, 2019, which claims priority to International Application No. PCT/IN2017/050560, filed on Nov. 30, 2017, which claims priority to Indian Application No. 201611041205, filed Dec. 2, 2016, and also claims priority to the Patent of Addition filed on Feb. 5, 2020 for Indian Application No. 202013004941, and all the benefits accruing therefrom under 35 U.S.C. § 119(a), the content of each of which is incorporated by reference in their entirety.

FIELD OF THE INVENTION

The present invention relates to a process for the photo-catalytic splitting of water using self-assembled metalloporphyrin 2D-sheets to form hydrogen and oxygen.

BACKGROUND AND PRIOR ART

Photocatalytic water splitting is one of the most promising methods to obtain sustainable and clean energy by utilizing solar energy. Seawater is the most abundant natural water source, has been rarely used for water splitting studies, instead of scarce pure water medium executed. The catalytic activity and stability of the photocatalysts are substantially reduced in seawater as compared to pure water. Therefore, the invention of a photocatalyst that operates perfectly with seawater is highly desirable for extensive practical application. Herein, report the first demonstration of solar-driven seawater splitting by a two-dimensional catalyst derived from metalloporphyrin bearing prepositioned phenolic functionalities. Although metalloporphyrins have received considerable recognition as the catalyst, a heterogeneous photocatalyst design efficiently performed on seawater medium not yet developed. A bimetallic (Co and Ni) porphyrin polymer exhibits significantly enhanced the bifunctional catalytic feature for $H_2$ and $O_2$ generation performance in pure water. It helps to extend the studies in seawater and river water. The excellent catalytic performance of the new catalyst showcasing long-term durability of 15 cycles in 200 days without a considerable decrease in efficiency. Deactivation modes of metalloporphyrin catalysts are inhibited by π-π stacking of layered porous polymer architecture, even in the stringent experimental condition, which signifies the molecular design of 2D-dimensional crystalline photocatalyst.

The Energy crisis and global warming are the greatest challenges for humanity in the 21st century, drives the focus on earth-abundant materials tailored for carbon-neutral fuel generation. Photocatalytic water splitting is a green and sustainable solution to energy and environmental issues by transforming abundant solar energy to clean chemical fuel in the form of hydrogen resulting in bringing an energy revolution. Even though many inorganic, organic systems and its composite have been tested for water splitting. It is notable that the most reachable natural water source, seawater has been rarely explored for hydrogen evolving reaction (HER) and oxygen-evolving reaction (OER); which profoundly restricts commercialization. It is due to the dissolved salts in seawater, mainly sodium chloride, would deplete the photo-generated charge carriers and cause unenviable side reactions on the catalyst surface. Therefore, the new catalyst design provides activity and stability in the experimental conditions is a real challenge. Apart from, photocatalysts struggle to promote OER because of the energetically up-hill O—O bond formation involves four-electron and four proton-coupled processes. Towards to obtain hydrogen via water splitting that is necessarily free of oxygen and of sufficient purity for use in industrial processes or in a fuel cell, systems in which O2 and H2 are created at separate points in space are necessary for both technological and safety measure point of view. Therefore, a catalyst that can selectively drive HER/OER depends on the condition; it is highly desirable for the energy conversion process.

Article titled "An efficient electrocatalyst for oxygen reduction reaction derived from a Co-porphyrin-based covalent organic framework" by Ma et al. published in Electrochemistry Communications; March 2015; 52, pp 53-57 reports a novel efficient electrocatalyst for oxygen reduction reaction (ORR) synthesized by pyrolysis of a cobalt-based covalent organic framework, which shows electrocatalytic performance comparable with the commercial Pt/C for ORR via an almost four-electron pathway in alkaline media without methanol-crossover effect.

The article titled "High-Performance Overall Water Splitting Electrocatalysts Derived from Cobalt-Based Metal-Organic Frameworks" by You et al. published in *Chem. Mater.*, 2015, 27 (22), pp 7636-7642 reports a facile two-step method to synthesize porous Co—P/NC nanopolyhedrons composed of $CoP_x$ (a mixture of CoP and $Co_2P$) nanoparticles embedded in N-doped carbon matrices as electrocatalysts for overall water splitting.

An efficient catalyst for splitting water to generate oxygen and hydrogen using solar energy is one of the demanding and cost-effective methods of renewable energy storage. However, even after several decades of research, a single durable material that works both as an effective photo and electrocatalyst for water splitting has rarely been attempted.

Therefore, there is a need to develop a process for a photo-catalytic splitting of seawater using self-assembled metalloporphyrin 2D-sheets. Accordingly, the inventors provide a process for the photocatalytic splitting of seawater using self-assembled metalloporphyrin 2D-sheets.

OBJECTIVE OF THE INVENTION

The objective of the present invention is to provide a process for the photocatalytic splitting of water using self-assembled metalloporphyrin 2D-sheets.

SUMMARY OF THE INVENTION

Accordingly, the present invention provides a process for the photocatalytic splitting of water using self-assembled metalloporphyrin 2D-sheets comprising:

a) dispersing the self-assembled metalloporphyrin 2D-sheets as a catalyst in water optionally adding cocatalyst and sacrificial reagent and stirring for 10 to 20 minutes followed by bubbling inert gas for 20 to 40 minutes to form a suspension;

b) stirring the entire suspension of step (a); and c) illuminating a light source on the suspension of step (b) to form hydrogen and oxygen, wherein said self-assembled metalloporphyrin 2D-sheet is represented by formula (I)

Formula (I)

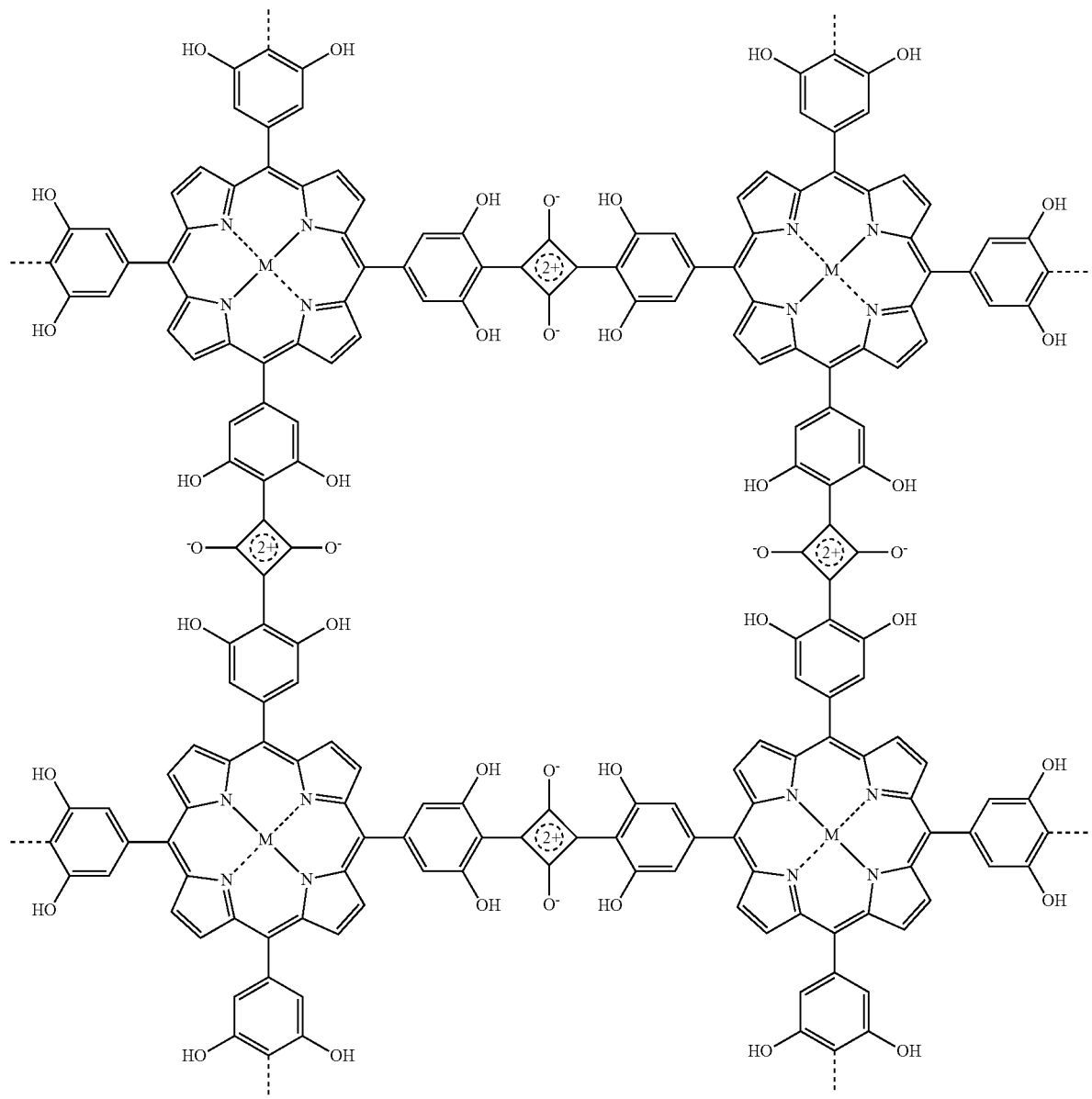

2DP1: M = Co
2DP2: M = Ni
2DP3A: M = Co/Ni (0.7:0.3)
2DP4: M = Zn wherein;

M is selected from cobalt, nickel, zinc, copper, iron, manganese, molybdenum or mixture thereof.

In one of the feature of the present invention, the self-assembled metalloporphyrin 2D-sheet is selected from 2DP1, 2DP2, 2DP3A, 2DP4 and mixture thereof.

In yet another feature of the present invention, said water is selected from seawater, river water, potable or non-potable water.

In still another feature of the present invention, said light source of step (c) is the visible light source, wherein the visible light source is selected from solar light, solar simulator and photoreactor.

In still another feature of the present invention, said catalyst is recycled and said catalyst shows long-term durability of 15 cycles in 200 days without a considerable decrease in efficiency.

In yet another feature of the present invention, said cocatalyst is in situ generated Pt cocatalyst from H2PtCl6 precursor.

In still another feature of the present invention, said sacrificial reagent is selected from silver nitrate or triethanolamine.

In yet another feature of the present invention, said process is hydrogen evolution reaction or oxygen evolution reaction, when said process is hydrogen evolution reaction, turn over number of hydrogen evolution reaction is 10.18 and when said the process is oxygen evolution reaction, turn over number of oxygen evolution reaction is 4.52.

In yet another feature of the present invention, said H2 is formed in the range of 1 to 2.1 μmol from the river or seawater.

In yet another feature of the present invention, said O2 is formed in the range of 0.1 to 0.8 μmol from the river or seawater.

BRIEF DESCRIPTION OF THE DRAWINGS

FIG. 1: a) Chemical structure of metalloporphyrin 2D-polymers 2DP1, 2DP2, 2DP3A, and 2DP4; b) Photocatalytic H2 (5 mg 2DP3A, 5 ml MeOH, 10 ml H2O) and O2 (5 mg 2DP3A, 10 ml H2O) evolution of 2DP3A with time under visible light irradiation (λ>420 nm) from pure water; c) Comparison of the H2 and O2 evolution performance of 2DP3A using various light sources such as A. photoreactor, B. solar simulator, C. sunlight; and d) Typical time course of H2 and O2 evolution from pure water by 2DP3A for 15 cycles over 200 days under visible light irradiation (λ>420 nm) using photoreactor.

FIG. 2: a) Chemical structure of a) Ni (II) metalloporphyrin 1b; b) Ni(II) 2D-polymer 2DP2; Photocatalytic H2 and O2 evolution of c) 1b; and d) 2DP2 in the absence of Ptcocatalyst (for HER: 5 mg catalyst, 5 ml TEoA, 10 ml H2O) and in the presence AgNO3 (for OER: 5 mg catalyst, 10 ml H2O, 1 mmol, 50 μl AgNO3) under visible light irradiation (λ>420 nm) using photoreactor for 6 h.

FIG. 3: Nyquist plots of Pt/C, 2DP3A, and 2DP1+2DP2 (7:3) in HER condition. The inset shows the equivalent circuit diagram.

FIG. 4: Photocatalytic H2 evolution of 2DP3A in the (a) absence and (b) presence of Pt cocatalyst under various visible light sources, 1. photoreactor, 2. solar simulator, 3. sunlight (5 mg 2DP3A, 5 ml TEoA, 10 ml H2O).

FIG. 5: Photocatalytic H2 and O2 evolution of physical mixture of 2DP1 and 2DP2 (7:3) in the absence of Pt (for HER) in the presence of AgNO3 (for OER) under visible light irradiation (λ>420 nm) using photoreactor.

FIG. 6: Photocatalytic a), b), c) H2 and d), e), f) O2 evolution of 2DP3A from different water sources in the absence of Pt cocatalyst (for HER) and in the presence of AgNO3 (for OER), illuminated with photoreactor, solar simulator, and sunlight, respectively.

FIG. 7: Comparison of the, a) HER and c), b) and d) OER yield for 2DP1 and 2DP2 in the optimized reaction conditions under visible light irradiation (λ>420 nm) using photoreactor for 6 h.

FIG. 8: Comparison of the HER and OER performance of all the catalysts used 2DP1, 2DP2, 2DP3A and 2DP4 along with a physical mixture of 2DP1 and 2DP2.

FIG. 9: a) HOMO and LUMO of the tetrad, and b) HOMO-LUMO gap for the various tetrads comprised of Co and Ni as the central metal ion calculated by semi-empirical calculation. c) Typical time course of H2 and O2 evolution from seawater by 2DP3A for 6 consecutive cycles under visible light irradiation (λ>420 nm) using photoreactor.

FIG. 10: a) and b) are the TEM images of 2DP3A after photocatalysis; c) TEM element mapping for N, O, Co and Ni of 2DP3A after cyclic photocatalytic water-splitting experiments. d) UV-Vis-NIR absorption and e) FT-IR spectra of 2DP3A before and after cyclic photocatalytic water-splitting experiments.

DETAILED DESCRIPTION OF THE INVENTION

The invention will now be described in detail in connection with certain preferred and optional embodiments, so that various aspects thereof may be more fully understood and appreciated.

The present invention provides a process for the photocatalytic splitting of water using self-assembled metalloporphyrin 2D-sheets comprising the steps of:
  a) dispersing the self-assembled metalloporphyrin 2D-sheets as a catalyst in water optionally adding cocatalyst and sacrificial reagents and stirring for 10 to 20 minutes followed by bubbling inert gas for 20 to 40 minutes to remove any dissolved oxygen to form the suspension;
  b) stirring the entire suspension of step (a) and
  c) illuminating the light source on the suspension of step (b) to form hydrogen and oxygen.

The dispersion can be carried out by sonication.

The inert gas is selected from nitrogen or argon.

The stirring of the suspension is carried out by magnetic stirrer.

The monitoring of the progress of the reaction is carried out by illuminating the visible light source i.e. solar light, solar simulator, and photoreactor.

The cocatalyst is Pt cocatalyst in situ generated from the $H_2PtCl_6$ precursor.

The sacrificial reagent is selected from silver nitrate ($AgNO_3$) or triethanolamine (TEoA).

The silver nitrate is used for the oxygen evolution reaction.
The triethanolamine is used for hydrogen evolution reaction.
The water is selected from sea-water, river water, potable or non-potable water.
The self-assembled metalloporphyrin 2D-sheets is represented by formula (I)
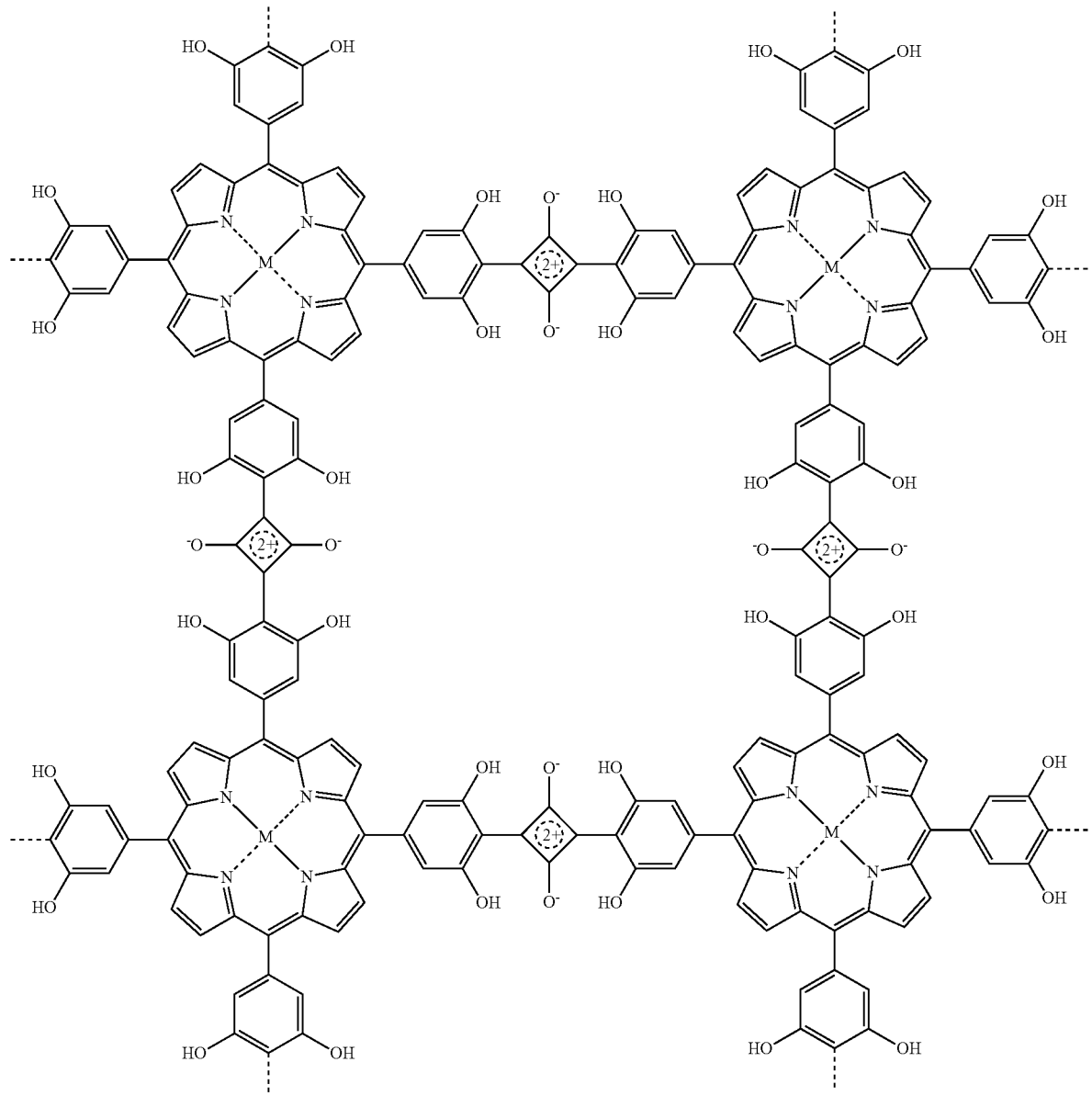
Formula (I)
2DP1: M = Co
2DP2: M = Ni
2DP3A: M = Co/Ni (0.7:0.3)
2DP4: M = Zn Wherein;

M is selected from cobalt, nickel, zinc, copper, iron, manganese, molybdenum or mixture thereof.

In the preferred embodiment, self-assembled metalloporphyrin 2D-sheets are selected from 2DP1, 2DP2, 2DP3A, 2DP4 and mixtures therefrom.

HER and OER experiments were carried out under steady-state conditions by headspace analysis at room temperature (25° C., normal atmospheric pressure). The catalyst was dispersed in water by sonication for 15 min. and subsequently, nitrogen gas was bubbled for 30 min. to remove any dissolved oxygen. During the course of the reaction, the entire suspension is stirred by using a magnetic stirrer. In general, 5 mg of the photocatalyst was suspended in an airtight quartz cell (closed with a silicone rubber septum) of 70 mL capacity containing 10 ml water and 5 ml of a sacrificial agent (for HER only) (55 ml dead volume). The progress of the reaction was monitored by illuminating various visible light sources such as photoreactor, solar simulator, and sunlight. Besides, approximately 45,000 and 50,000 lux was confirmed before each photoreactor and sunlight illumination experiments, respectively. The headspace of the reactor was periodically sampled with an offline injection system by a gas phase syringe having an injection volume of 500 µl. The gas analysis was carried out by regular sampling every hour and a gas chromatograph (GC) equipped with a TCD detector (Agilent 7890) was employed for quantitative analysis. After a saturation regime in the first cycle, the photocatalyst suspension is purged with $N_2$ for 30 min before starting the next cycle and for repeated experiments, the catalyst is filtered after each photocatalytic cycle, washed with excess methanol and dried under vacuum.

The excellent catalytic performance of the new catalyst showed a long-term durability of 15 cycles in 200 days without a considerable decrease in efficiency.

The significance of molecular design and the effect of the central metal ion in tuning $H_2$ evolution is investigated with the finding that a bimetallic (Co and Ni) porphyrin polymer significantly enhanced the performance for the electrocatalytic HER The successful results of metalloporphyrin two-dimensional polymers in electrocatalysis and the preliminary results of photocatalysis impel inventor to undertake new challenges such as improve photocatalytic HER/OER, in addition, develop a catalyst active even in natural water resources. FIG. 2 depicts photocatalytic $H_2$ and $O_2$ evolution of (A) 1b and (B) 2DP2 in the absence of Pt cocatalyst (for HER: 5 mg catalyst, 5 ml TEoA, 10 ml $H_2O$) and in the presence $AgNO_3$ (for OER: 5 mg catalyst, 10 ml $H_2O$, 1 mmol, 50 µl $AgNO_3$) under visible light irradiation (λ>420 nm) using photoreactor for 6 h, however, no significant improvement in Photocatalytic HER/OER is observed. Both HER and OER reached saturation in 4-6 hours (h) under photoreactor illumination yielded 0.46 µmol/g of $H_2$ and 0.27 µmol of $O_2$. To have a comparison with molecular catalyst 1b, executed the HER and OER experiments in the optimized conditions resulted in 0.15 µmol and 0.025 µmol respectively. FIG. 3 depicts Nyquist plots of Pt/C, 2DP13A, and 2DP1+2DP2 (7:3) in HER condition. The inset shows the equivalent circuit diagram. Bimetallic (Co and Ni) porphyrin polymer, 2DP3A best-performing catalyst in the electrocatalytic HER due to specific combination of active centers, has least charge transfer resistance (Rct) (214Ω) among all the 2D-polymer catalysts tested and is closer to Pt/C according to the electrochemical impedance spectroscopy results. Compared to 2DP1 and 2DP2, new catalyst exhibited improved HER activity in presence of TEoA sacrificial donor in $H_2O$, even without Pt cocatalyst while retaining almost the same OER performance with assistance from $AgNO_3$ (FIGS. 1 and 4). FIG. 4 depicts photocatalytic $H_2$ evolution of 2DP3A in the (A) absence and (B) the presence of Pt cocatalyst under various visible light sources, 1. photoreactor, 2. solar simulator, 3. sunlight (5 mg 2DP3A, 5 ml TEoA, 10 ml $H_2O$). The performance of 2DP3A also varied with the light source and it generated 450 µmol/g of $H_2$ in aqueous TEoA solution and 1 µmol of $O_2$ under direct sunlight (FIG. 1). 2DP3A in combination of TEoA as sacrificial electron donor and in situ formed Ptcocatalyst; integrated by addition $H_2PtCl_6$ (50 µL, 1 wt % in $H_2O$) as precursor not appreciably improved the HER; It released 1.95 µmol of $H_2$ in the presence of Pt cocatalyst and 0.46 µmol of $O_2$ in the absence of $AgNO_3$ upon photoreactor illumination (FIG. 4).

In 2DP3A M=Co/Ni (0.7:0.3), while it is covalently bonded single framework. Yet 2DP1, 2DP2 pure polymers physically mixed to make 2DP1+2DP2 (0.7:0.3) ratio in order to validate the synergism arising from covalently linked 2DP3A compared to 2DP1 and 2DP2 physical mixtures even though relative metal centres ratios are same.

After the saturation regime in the first cycle, the photocatalyst suspension was purged with $N_2$ for 30 min before the next cycle. In cyclic experiments, the catalyst is filtered after each photocatalytic cycle, washed with excess methanol and dried under vacuum. HER and OER performance of 2DP3A is impressive and highest among metalloporphyrins and other 2D polymer-based catalysts. Even after 15 cycles over 200 days under photoreactor illumination, the same 2DP3A sample retained HER and OER efficiency within the error limit and the performance of the catalyst is still being monitored (FIG. 1c). FIG. 5 depicts Photocatalytic $H_2$ and $O_2$ evolution of physical mixture of 2DP1 and 2DP2 (7:3) in the absence of Pt(for HER) in the presence of $AgNO_3$ (for OER) under visible light irradiation (λ>420 nm) using photoreactor. 2DP3A showcases excellent photocatalytic HER and OER with minimum additives due to the synergistic effect of the two catalytic metal centers present in the same 2D-sheet, which is not observed in the case of a physical mixture of 2DP1 and 2DP2 (7:3) (FIG. 5).

Bimetallic (Co and Ni) porphyrin polymer, 2DP3A exhibits remarkably enhanced performance for the Photocatalytic HER without the assistance of the cocatalyst. The light-driven hydrogen evolution of 2DP3A from river and seawater was evaluated under irradiation under visible light irradiation (λ>420 nm) by using photoreactor) with TEOA as sacrificial hole scavengers (River-Sea water/TEOA, 2:1 v/v) in the absence of Pt cocatalyst (for HER).

Photocatalytic OER experiments in the presence of $AgNO_3$ as sacrificial agents in river water and seawater 0.25 µmol and 0.2 µmol of $O_2$ generated respectively. Photocatalytic cyclic experiments and river and seawater tests for both HER and OER confirmed the importance of a self-assembled porous platform to show excellent catalytic activity compared to molecular catalysts 1a and 1b. The improved OER and HER performance of 2DP3A might be attributed to a complete balance of conductivity, active catalytic sites, and porosity of the polymer sheets.

The light-driven $H_2$ evolution of 2DP3A from river and seawater was evaluated under visible light irradiation (λ>420 nm) by using photoreactor with TEOA as a sacrificial hole scavenger (river, seawater/TEOA, 2:1 v/v) in the absence of Pt cocatalyst (for HER). The result showed that 2DP3A generated 1.28 and 1.04 µmol of $H_2$ respectively from the river and seawater (FIG. 6a). As demonstrated in FIG. 6a, gas evolution attains saturation in the evolution rate by 6 hours. OER experiments in the presence of $AgNO_3$ as a sacrificial agent in river water and seawater resulted in 0.48 and 0.37 µmol of $O_2$, respectively (FIG. 6d). Both HER and OER experiments in river and seawater were repeated under light illumination with the solar simulator and 2DP3A exhibited an enhanced $H_2$ and $O_2$ evolution (FIGS. 6b and 6e). Sunlight exposure released 2.06 and 1.64 µmol of $H_2$ and 0.80 and 0.61 µmol of $O_2$ from the river and sea waters, respectively (FIGS. 6c and 6f).

The turnover number for 2DP3A was found to be 10.1 (HER) without the assistance of any cocatalyst and 4.5 (OER) by the photocatalytic oxidation of water with $AgNO_3$ sacrificial electron acceptor under direct sunlight illumination, assuming that all-metal centers participate in catalysis. Turn Over Number (TON)

TON=moles of evolved $H_2$/moles of catalyst used.

TON for 2DP3A under direct sunlight condition, where: 2.26 µmol of $H_2$ and 0.95 µmol of $O_2$ evolution was observed. All the Co metal centers (obtained from MP-AES analysis) are assumed to be active in catalysis for TON calculation.

HER: $2.6 \times 10^{-6}$ mol/$2.4604 \times 10^{-7}$ mol=10.18
OER: $0.95 \times 10^{-6}$ mol/$2.4604 \times 10^{-7}$ mol=4.52

HER, OER yield for 2 DP1 and 2DP2 in the optimized reaction conditions under visible light irradiation ($\lambda$>420 nm) using photoreactor for 6 h. 0.365, 0.295, 0.235 µmol of $H_2$ and 0.475, 0.37, 0.315 µmol of $O_2$ released by 2 DP1 invisible light irradiation ($\lambda$>420 nm) by using photoreactor from pure water, river water seawater respectively. 2DP2 evolved 0.645, 0.55, 0.486 µmol of $H_2$ and 0.29, 0.235, 0.18 µmol of $O_2$ in the visible light irradiation ($\lambda$>420 nm) by using photoreactor from pure water, river water seawater respectively (FIG. 7).

FIG. 8 depicts a comparison of the HER and OER performance of all the catalysts used 2DP1, 2DP2, 2DP3A and 2DP4 along with a physical mixture of 2DP1 and 2DP2 clearly demonstrate the significance of the bimetallic catalyst design of 2DP3A having synergism between the active sites.

Semiempirical calculations for a tetrad of the monomers connected by dicationic 1,3-cyclobutanedione units to expand the electron conjugation, with varying Co and Ni ratio shows that the compared to $Co_4$ and $Ni_4$, the mixed combinations exhibit lower HOMO-LUMO gap (FIGS. 9a, 9b). Among the series given in FIG. 9b, tetrad $Co_2:Ni_2$ trans has the lowest HOMO-LUMO gap. Hence it is assumed that a combination of $Co_2:Ni_2$ trans in the tetrad shows the highest catalytic activity as compared to the tetrads of Co or Ni alone (FIG. 9b). However, the preparation of $Co_2:Ni_2$ always results in a mixture of both cis and trans and imparts a less catalytic activity than $Co_3:Ni_1$. The semi-empirical calculation provides a qualitative idea of the activity trend and indicated that the highest reactivity to be co-related to the least stability as seen from the lowest bandgap in the $Co_3:Ni_1$ polymer. This implies a qualitative picture of the energy levels and corresponding correlation with the comparatively better catalytic performance of 2DP3A in the series.

Prior art photocatalysts are inconsistent and show a constant drop in catalytic performance in periodic experiments. However, the present design of catalyst capacitates to overcome it. The stability of the photocatalyst 2DP3A on continuous experimentation was investigated by several experiments such as the structural stability of the catalyst in repeated catalytic cycles, rate of $H_2$ and $O_2$ evolution over time, mass loss or gain after the long-term operation, gases released during operation, etc. All these experiments point to the supportive role of the 2D-polymer platform to impart durability and reliable performance. In order to check the stability of the catalyst under repeated photocatalytic experiments, cyclic OER and HER experiments in seawater were conducted (FIG. 9c). Even after 6 cycles, the same catalyst sample with optimized conditions (FIG. 9c), retained the same efficiency within the error limit. In the cyclic experiments also no gases other than $H_2$ and $O_2$ are observed in gas chromatograms. The weight loss of the catalyst after the photocatalytic reaction cycles was checked and found negligible mass loss or gain. FIG. 10 depicts TEM images of 2DP3A after Photocatalysis which retains the morphology before using for catalysis. It validates the stability of the material. TEM image showed that the same layered morphology with porous features (FIGS. 10a and 10b) and elemental composition is retained as proved by TEM elemental mapping after repeated water-splitting experiments (FIG. 10c). Solid-state UV-Vis-NIR spectra (FIG. 10d) and Fourier-transform infrared spectra (FIG. 10e) of the 2DP3A catalyst remain consistent even after repeated photocatalytic reactions and illustrate its structural stability.

All the control experiments point to the structural stability of the catalysts and thus find useful for long-term photocatalytic water splitting cycles. 2DP3A is the first porphyrin-based bifunctional heterogeneous photocatalyst, exhibiting $H_2$ evolution in the absence of cocatalyst and $O_2$ evolution in natural water resources.

The following examples, which include preferred embodiments, will serve to illustrate the practice of this invention, it being understood that the particulars shown are by way of example and for purpose of illustrative discussion of preferred embodiments of the invention.

EXAMPLES

Following examples are given by way of illustration and therefore should not be construed to limit the scope of the invention.

Example 1: Splitting of Water

HER and OER experiments were carried out under steady-state conditions by headspace analysis at room temperature (25° C., normal atmospheric pressure). The catalyst was dispersed in water by sonication for 15 min. and subsequently, nitrogen gas was bubbled for 30 min. to remove any dissolved oxygen. During the course of the reaction, the entire suspension is stirred by using a magnetic stirrer. In general, 5 mg of the photocatalyst was suspended in an airtight quartz cell (closed with a silicone rubber septum) of 70 mL capacity containing 10 ml Sea or river water and 5 ml of triethanolamine (for HER) (55 ml dead volume) or 50 µl of $AgNO_3$ (for OER). The progress of the reaction was monitored by illuminating various visible light sources such as photoreactor, solar simulator, and sunlight. Optionally Pt Cocatalyst in situ generated from (50 µL, 1 wt % in $H_2O$) $H_2PtCl_6$ precursor for HER Approximately 45,000 and 50,000 lux was confirmed before each photoreactor and sunlight illumination experiments, respectively. The headspace of the reactor was periodically sampled with an offline injection system by a gas phase syringe having an injection volume of 500 µl. The gas analysis was carried out by regular sampling every hour and a gas chromatograph (GC) equipped with a TCD detector (Agilent 7890) was employed for quantitative analysis. After a saturation regime in the first cycle, the photocatalyst suspension is purged with $N_2$ for 30 min before starting the next cycle and for repeated experiments, the catalyst is filtered after each photocatalytic cycle, washed with excess methanol and dried under vacuum.

ADVANTAGES OF INVENTION

2DP3A is the first porphyrin-based bifunctional heterogeneous photocatalyst, exhibiting $H_2$ evolution in the absence of cocatalyst and $O_2$ evolution in natural water resources.

Seawater, the most accessible natural water source was used.

Exhibits efficient seawater splitting and delivers hydrogen and oxygen.

We claim:
1. A process for the photocatalytic splitting of water using self-assembled metalloporphyrin 2D-sheets, the process comprising:
   a) dispersing the self-assembled metalloporphyrin 2D-sheets as a catalyst in water, optionally adding a cocatalyst and a sacrificial reagent and stirring for 10 to 20 minutes followed by bubbling an inert gas for 20 to 40 minutes to form a suspension;
   b) stirring the suspension of step (a); and
   c) illuminating a light source on the suspension of step (b) to form hydrogen and oxygen, wherein said self-assembled metalloporphyrin 2D-sheet is represented by formula (I)

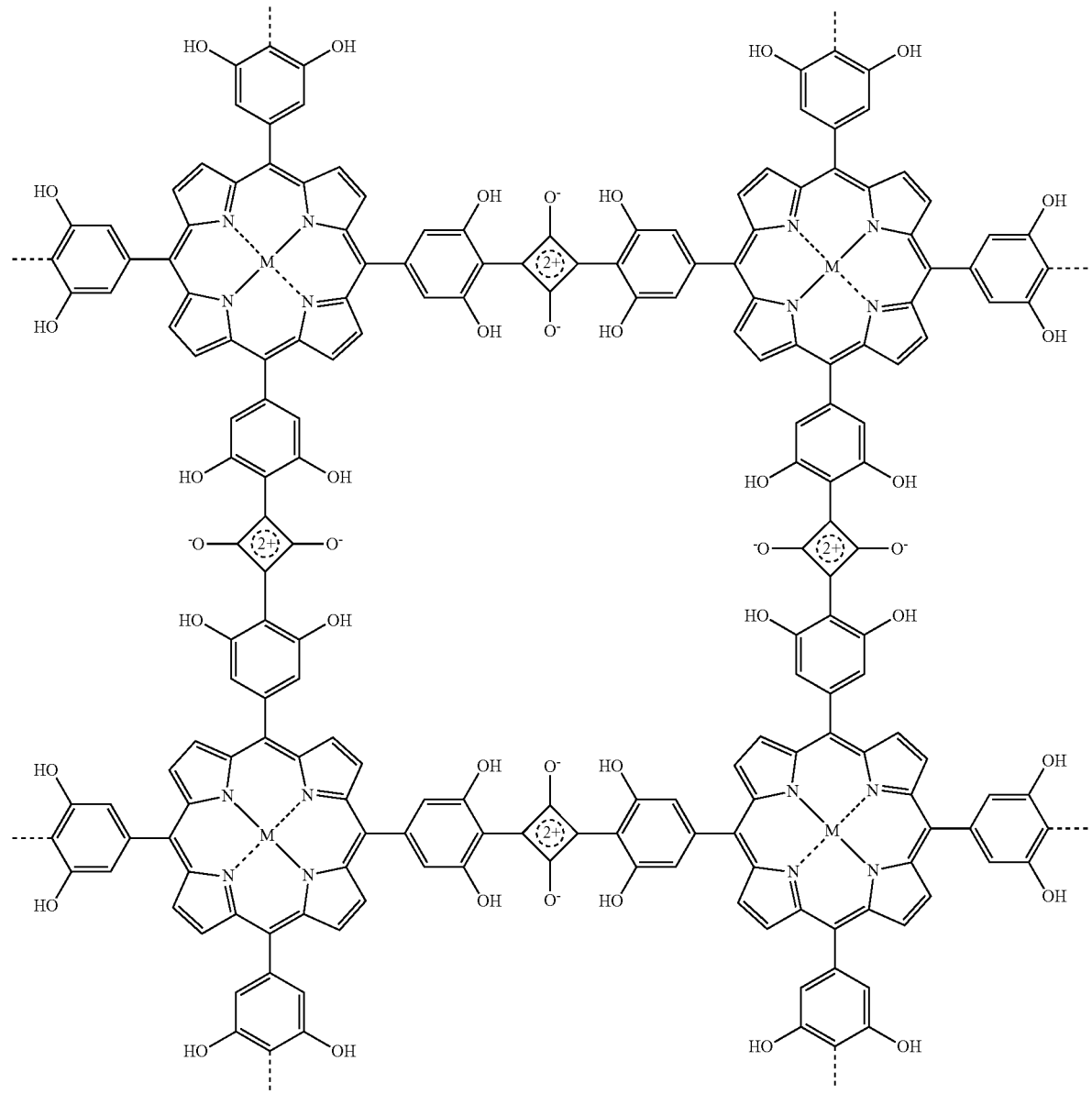

Formula (I)

2DP1: M = Co
2DP2: M = Ni
2DP3A: M = Co/Ni (0.7:0.3)
2DP4: M = Zn wherein M is selected from cobalt, nickel, zinc, copper, iron, manganese, molybdenum or mixture thereof.

2. The process as claimed in claim 1, wherein said self-assembled metalloporphyrin 2D-sheet is selected from 2DP1, 2DP2, 2DP3A, 2DP4, and mixtures thereof, wherein when M is cobalt, the self-assembled metalloporphyrin 2D-sheet is 2DP1; when M is nickel, the self-assembled metalloporphyrin 2D-sheet is 2DP2; when M is cobalt and nickel in a ratio of 0.7:0.3, the self-assembled metalloporphyrin 2D-sheet is 2DP3; and when M is zinc, the self-assembled metalloporphyrin 2D-sheet is 2DP4.

3. The process as claimed in claim 1, wherein said water is selected from seawater, river water, potable, and non-potable water.

4. The process as claimed in claim 1, wherein said light source of step (c) is a visible light source, wherein the visible light source is selected from a solar light, a solar simulator and a photoreactor.

5. The process as claimed in claim 1, wherein said catalyst is recycled and said catalyst shows long-term durability of 15 cycles in 200 days without a considerable decrease in efficiency.

6. The process as claimed in claim 1, wherein said cocatalyst is a Pt cocatalyst generated in situ from a H2PtCl6 precursor.

7. The process as claimed in claim 1, wherein said sacrificial reagent is selected from silver nitrate and triethanolamine.

8. The process as claimed in claim 1, wherein said process is a hydrogen evolution reaction or an oxygen evolution reaction, and when said process is a hydrogen evolution reaction, the turn over number of hydrogen evolution reaction is 10.18 and when the process is an oxygen evolution reaction, the turn over number of oxygen evolution reaction is 4.52.

9. The process as claimed in claim 3, wherein said hydrogen is formed in the range of 1 to 2.1 μmol from the river water or seawater.

10. The process as claimed in claim 3, wherein said oxygen is formed in the range of 0.1 to 0.8 μmol from the river water or seawater.

* * * * *